(12) United States Patent
Correns et al.

(10) Patent No.: US 10,299,674 B2
(45) Date of Patent: May 28, 2019

(54) VISUAL FIELD MEASURING DEVICE AND SYSTEM

(71) Applicants: Carl Zeiss Meditec AG, Jena (DE); Carl Zeiss Meditec, Inc., Dublin, CA (US)

(72) Inventors: Nico Correns, Weimar (DE); Hans-Jürgen Dobschal, Kleinromstedt (DE); Elke Machalett, Jena (DE)

(73) Assignees: Carl Zeiss Meditec AG, Jena (DE); Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 15/512,570

(22) PCT Filed: Sep. 22, 2015

(86) PCT No.: PCT/EP2015/071726
§ 371 (c)(1),
(2) Date: Mar. 19, 2017

(87) PCT Pub. No.: WO2016/046202
PCT Pub. Date: Mar. 31, 2016

(65) Prior Publication Data
US 2017/0290505 A1    Oct. 12, 2017

(30) Foreign Application Priority Data
Sep. 22, 2014  (DE) .......................... 10 2014 113 682

(51) Int. Cl.
*A61B 3/024* (2006.01)
*A61B 3/00* (2006.01)

(52) U.S. Cl.
CPC ............ *A61B 3/024* (2013.01); *A61B 3/0033* (2013.01)

(58) Field of Classification Search
CPC ....... A61B 3/032; A61B 3/0091; A61B 3/024; A61B 3/028; A61B 3/0033; A61L 33/0033
USPC .................................................. 351/200–246
See application file for complete search history.

(56) References Cited

U.S. PATENT DOCUMENTS

| | | |
|---|---|---|
| 5,026,151 A | 6/1991 | Waltuck et al. |
| 5,550,602 A | 8/1996 | Braeuning |
| 5,565,949 A | 10/1996 | Kasha, Jr. |
| 5,737,060 A | 4/1998 | Kasha, Jr. |
| 5,864,384 A | 1/1999 | McClure et al. |
| 5,880,812 A | 3/1999 | Solomon |
| 5,898,474 A | 4/1999 | McClure et al. |
| 5,910,834 A | 6/1999 | McClure et al. |

(Continued)

FOREIGN PATENT DOCUMENTS

| | | |
|---|---|---|
| DE | 43 26 760 A1 | 3/1995 |
| DE | 195 02 337 A1 | 8/1996 |

(Continued)

OTHER PUBLICATIONS

International Search Report and Written Opinion for PCT/EP2015/071726, dated Nov. 1, 2016, 9 pages.

(Continued)

*Primary Examiner* — Mohammed A Hasan
(74) *Attorney, Agent, or Firm* — Patterson Thuente Pedersen, P.A.

(57) ABSTRACT

The invention relates to mobile computer devices, front-mounted optical systems and computer program products allowing perimetry measurement.

24 Claims, 4 Drawing Sheets

(56) References Cited

U.S. PATENT DOCUMENTS

| | | |
|---|---|---|
| 5,920,374 A | 7/1999 | Vaphiades et al. |
| 6,027,217 A | 2/2000 | McClure et al. |
| 6,033,076 A | 3/2000 | Braeuning et al. |
| 6,045,227 A | 4/2000 | Stewart et al. |
| 6,145,991 A | 11/2000 | McClure et al. |
| 6,149,272 A | 11/2000 | Bergner et al. |
| 6,290,357 B1 | 9/2001 | Massengill et al. |
| 6,386,706 B1 | 5/2002 | McClure et al. |
| 6,592,222 B2 | 7/2003 | Massengill et al. |
| 6,656,131 B2 | 12/2003 | Alster et al. |
| 7,350,921 B2 | 4/2008 | Ridings |
| 7,367,671 B2 | 5/2008 | Sabel |
| 7,446,941 B2 | 11/2008 | Fukuda |
| 7,448,751 B2 | 11/2008 | Kiderman et al. |
| 7,682,021 B2 | 3/2010 | Sabel |
| 7,740,592 B2 | 6/2010 | Graham et al. |
| 7,753,524 B2 | 7/2010 | Sabel |
| 7,972,278 B2 | 7/2011 | Graham et al. |
| 8,075,134 B2 | 12/2011 | Tanassi et al. |
| 8,333,475 B2 | 12/2012 | Sugio et al. |
| 8,668,334 B2 | 3/2014 | Krenik |
| 9,186,293 B2 | 11/2015 | Krenik |
| 9,743,828 B2 | 8/2017 | Bartlett et al. |
| 2004/0057013 A1* | 3/2004 | Cappo ................ A61B 3/024 351/224 |
| 2004/0141152 A1 | 7/2004 | Marino et al. |
| 2005/0124375 A1 | 6/2005 | Nowosielski |
| 2007/0200927 A1 | 8/2007 | Krenik |
| 2008/0079902 A1 | 4/2008 | Mandelstam-Manor et al. |
| 2009/0153796 A1 | 6/2009 | Rabner |
| 2010/0118264 A1 | 5/2010 | Sabel |
| 2010/0292999 A1 | 11/2010 | Verma |
| 2011/0267577 A1 | 11/2011 | Verma |
| 2012/0133890 A1* | 5/2012 | Rathjen ................ A61B 3/024 351/209 |
| 2012/0307203 A1* | 12/2012 | Vendel ................ A61B 3/085 351/201 |
| 2013/0090938 A1 | 4/2013 | Fishman et al. |
| 2013/0128223 A1* | 5/2013 | Wood ................ A61B 5/0077 351/206 |
| 2013/0141697 A1 | 6/2013 | Berry et al. |
| 2013/0155376 A1 | 6/2013 | Huang et al. |
| 2014/0085282 A1 | 3/2014 | Luebke et al. |

FOREIGN PATENT DOCUMENTS

| | | |
|---|---|---|
| DE | 195 40 802 A1 | 5/1997 |
| EP | 2742851 A1 | 6/2014 |
| EP | 2742852 A1 | 6/2014 |
| EP | 2796088 A1 | 10/2014 |
| JP | S63 49129 A | 3/1988 |
| JP | 4169881 | 2/2001 |
| JP | 2005-278670 A | 10/2005 |
| JP | 2009-268778 A | 11/2009 |
| JP | 2011-224213 A | 11/2011 |
| JP | 5141522 | 11/2012 |
| WO | WO 98/02083 | 1/1998 |
| WO | WO 02/31580 A1 | 4/2002 |

OTHER PUBLICATIONS

English translation of International Search Report for PCT/EP2015/071726, dated Nov. 1, 2016, 2 pages.
DE Search Report for DE 10 2014 113 682.9, dated Oct. 6, 2015, 9 pages.
Wang, Yi-Zhong, et al,: Handheld shape discrimination hyperacuity test on a mobile device for remote monitoring of visual function in maculopathy. In: Investigative ophthalmology & visual science, 2013, 54. Jg., Nr. 8, S. 5497.

* cited by examiner

VISUAL FIELD MEASURING DEVICE AND SYSTEM

RELATED APPLICATIONS

The present application is a National Phase entry of PCT Application No. PCT/EP2015/071726, filed Sep. 22, 2015, which claims priority from DE Patent Application No. 10 2014 113 682.9, filed Sep. 22, 2014, said applications being hereby incorporated by reference herein in their entirety.

FIELD OF THE INVENTION

The present application concerns a device for the measurement of the visual field (perimetry), an optical attachment for this purpose and a corresponding computer program product.

BACKGROUND

Perimetry is a procedure to examine a visual field of a person. The visual field of a single eye thereby extends towards the temple up to approx. 90 degrees, towards the nose and upwards to about 60 degrees and downwards to about 70 degrees. The different expansion is provided by the protected location of the eye in the eye socket. Towards the nose, the nasal bridge restricts the visual field, upwards and downwards the orbital margin, while the side of the temple is essentially free.

The visual field of the right and left eye overlaps in the middle. This overlapping covers an angle of about 120 degrees. A depth perception (stereo vision) is only possible in the area of the overlap.

In perimetry, light stimuli are then usually provided by a special device (perimeter) in different areas of the visual field of a person to be examined, while the person focuses her eyes or an eye to be examined on a fixed point and evaluates a reaction of the person (e.g. a confirmation of the perception of the light stimulus). Such light stimuli may have different brightness levels.

Such conventional perimeters require a lot of space, are comparatively expensive, and/or require skilled personnel to operate them.

SUMMARY OF THE INVENTION

Embodiments of the invention provide devices for the measurement of the visual field that are comparatively compact and inexpensive and/or enable a simple operation by a respective user.

According to a first aspect, a mobile computer device is provided, comprising:
a display,
a processor,
and
a memory with a program code stored therein,
wherein the program code, when executed on the processor, has the effect that the processor actuates the display to show light stimuli to perform a measurement of a visual field.

The mobile computer device may further comprise an input device and/or can be connected with an input device, wherein the program code, when executed on the processor, can furthermore effect that the processor determines the visual field based on a response by the user through the input device in answer to the display of the light stimuli.

The light stimuli are variable with regard to shape, size, color, brightness, and/or contrast.

The mobile computer device may furthermore comprise a camera, and/or can be connected with a camera, wherein the mobile computer device can be configured to determine a viewing direction of a user on the basis of the camera image.

The mobile computer device may be configured to perform the determination of the visual field depending on the specific viewing direction.

The mobile computer device may furthermore comprise a network interface to exchange data with medical staff.

The program code, when executed on the processor, can have the effect that an image for a left eye of a user is displayed on a first part of the display and that an image for a right eye is displayed on a second part of the display.

The mobile computer device may comprise a Smartphone or a tablet computer.

A rear or a frontal camera integrated in a housing of the Smartphone or the tablet computer can be configured to measure an ambient light when measuring the visual field.

The mobile computer device may be configured to determine by use of a luminance captured by a rear or frontal camera, whether the measurement of the visual field is feasible.

According to a second aspect, a mobile computer device is provided, comprising:
a display and structure to control the display such that the display shows light stimuli to perform the measurement of a visual field.

The mobile computer device may further comprise an input unit and/or can be connected with an input unit, wherein the mobile computer device comprises structure to determine the visual field based on a response by the user through the input device in answer to the display of the light stimuli.

The mobile computer device may further comprise a camera and/or can be connected with a camera, wherein the mobile computer device may be configured to determine a viewing direction of a user on the basis of the camera image.

Optional features of the first aspect may also be implemented in the second aspect.

According to a third aspect, an optical attachment is provided for the connection with a mobile computer device, wherein the optical attachment is configured to transfer an image displayed on one display of the mobile computer device with defined angle ratios and/or in a preferably three-dimensional visual field for at least one eye of a user.

"With defined angle ratios" can thereby mean, in particular that a respective image point of the display, when it is bright, for example, will illuminate the eye from a clearly assigned predefined angle to be able to thus scan a visual field, for example.

The optical attachment may be configured to transfer the image to at least one virtual hemisphere.

The virtual hemisphere can have a radius of between 350 mm and 400 mm.

The virtual hemisphere can have a radius of between 350 mm and 600 mm.

The virtual hemisphere can have a radius of more than 400 mm.

The optical attachment can comprise a concave surface to display the image for the eye.

The optical attachment can also comprise a first concave surface to display a first part of the image for a first eye and a second concave surface to display a second part of the image for a second eye.

The optical attachment can comprise a hologram, a volume hologram and/or a fiber optic.

A system is furthermore provided, comprising: a mobile computer device according to the first or second aspect, and an optical attachment connected with a display of the mobile computer device according to the third aspect.

The system can essentially be connected light-tight with a head of a user.

The system can be fixable relative to a head of a user.

According to a fourth aspect, a computer program product to determine a visual field is provided with a program code which, if executed on a processor, has the effect that the processor actuates a display to show light stimuli to perform a measurement of a visual field.

In particular, the computer program product can serve the implementation of the first or second aspect.

According to the invention, a mobile computer device, for example a Smartphone, a tablet computer, or another mobile computer device may be used for a perimetry measurement. The possibilities, comprising such mobile computer devices such as an integrated camera, installed communication protocols (WLAN, Blue tooth, mobile phone network, etc.) and a display of the mobile computer device can thereby be used. A device per the invention can thus be realized in a comparatively inexpensive manner.

According to another aspect, a procedure is provided to measure a visual field, which is executed by a device or a system according to an aspect or an execution example.

The procedure may comprise an output of light stimuli to perform the visual field measurement, wherein the light stimuli are output through a display of a mobile computer device.

The procedure may comprise a transferring of an image shown on the display of the mobile computer device by use of an optical attachment connected to the display of the mobile computer device, which transfers the image with defined angle ratios and/or in a preferred three-dimensional visual field for an eye of a user.

The procedure may comprise a reversibly detachable recording of the mobile computer device by use of a housing that the optical attachment is installed in.

The procedure may comprise a measure of ambient light through a camera of the mobile computer device to determine whether the measurement of the visual field is feasible.

BRIEF DESCRIPTION OF THE DRAWINGS

The invention is further described below by example embodiments with reference to the enclosed drawings. The following is shown.

In the following, different example embodiments of the invention are described in detail with reference to the enclosed drawings. These example embodiments merely serve illustrative purposes and are not to be interpreted as restrictive. For example, a description of an example embodiment with a multitude of elements or features does not mean that all these elements or features are necessary for the implementation of example embodiments. Other example embodiments may rather have less features or elements, alternative features or elements and/or additional features or elements. Features or elements from different example embodiments may additionally be combined with each other unless stated otherwise.

DETAILED DESCRIPTION

Figure 1:
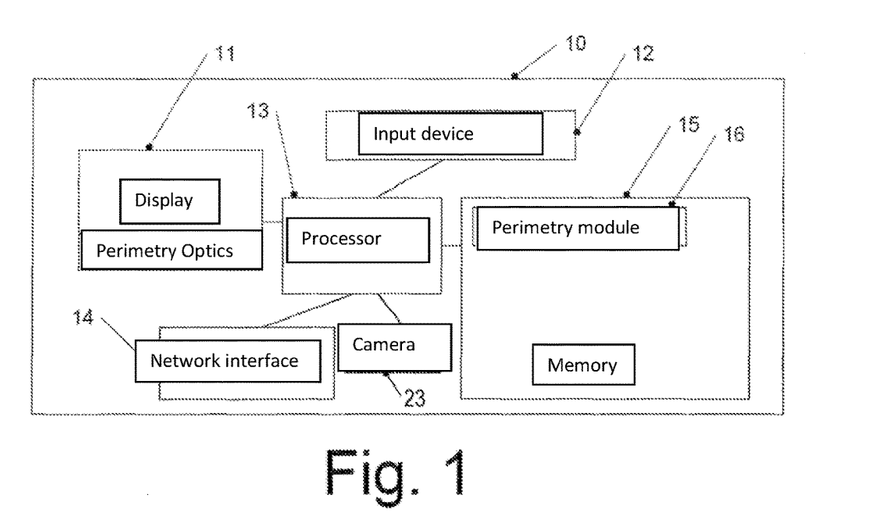
FIG. 1 a block diagram of a device according to an example embodiment.

FIG. 1 shows a mobile computer device 10 according to an example embodiment. The mobile computer device 10 may be implemented by use of a Smartphone, a tablet computer, or by use of another mobile computer device (such as a mobile game device), for example. Such mobile computer devices, which can serve as the basis for the implementation of the mobile computer device 10 of FIG. 1, are often freely programmable, have a processor, a display (display possibly touch-sensitive), different input devices, network interfaces, etc. As is clarified below, such mobile computer devices are used in example embodiments of the present invention to provide diagnostic possibilities to measure a visual field (perimetry). In particular, the mobile computer device can be programmed here accordingly, for example by use of one or several so-called apps (from the English "applications", meaning user programs).

As an example, the mobile computer device of FIG. 1 comprises a processor 13, for instance a CPU. In other example embodiments, several processors or one processor with several processor cores may also be provided. The processor 13 is connected with a memory 15, for example a memory with a random access (RAM), or a non-volatile memory such as a flash memory or combinations thereof. Data and programs to operate the processor 13 and the mobile computer device 10 may be stored in the memory 15. In particular, different application programs (apps) may be stored in the memory, for example an application program module 16 which is discussed in greater detail later on.

The processor 13 is further connected to a display 11 through which information, images, graphics and the like can be displayed for viewing by a user. Moreover, the processor 13 is connected to an input device 12. In some examples, the display 11 can be touch-sensitive and can thus simultaneously represent the input device 12 or a part thereof. Additionally or alternatively, the input device may comprise buttons, knobs, a keyboard, a microphone to receive noise or a voice input and/or sensors such as an inclination sensor or an acceleration sensor. In other execution examples, the input device 12 may additionally or alternatively comprise one or several cameras.

The mobile computer device 10 of FIG. 1 furthermore comprises a network interface 14, by which the computer device 10 can communicate with further devices. The network interface 14 can serve the data exchange and may, for example, comprise a mobile phone interface for communication through a mobile phone network, a Bluetooth interface or a Wi-Fi/WLAN interface, is however not limited to it. It must be noted that the mobile computer device 10 may comprise more conventional components of mobile computer devices such as Smartphones, for example.

In the example shown, a perimetry module 16 is stored in the memory 15 as application programs. In other examples, other modules can also still be provided, which optionally also interact with each other, particularly can exchange data.

The perimetry module 16 serves to perform a diagnosis function to measure a visual field (perimetry) of a user by application of the mobile computer device 10. This is explained in more detail later on.

Results of such a perimetry can also be sent through the network interface 14 to provide them to medical professionals such as a doctor or an optician for control and inspection, for example.

With such a mobile computer device, treatments and measurements during controlled lighting conditions are possible in example embodiments. Many displays of today's Smartphones or tablets have a high dynamic range. This enables measurements such as perimetry measurements with a very high contrast range. For example, displays on the basis of organic light-emitting diodes (OLED) have a contrast range of 1,000:1 or more.

The rear camera and the frontal camera provided in Smartphones or tablets allow for a measurement of the ambient light. It can thus be determined whether measurements must be discarded, for example, because the ambient light is too strong, or whether measurements may have a high confidence assigned to them because the ambient light is weak.

Figure 2:
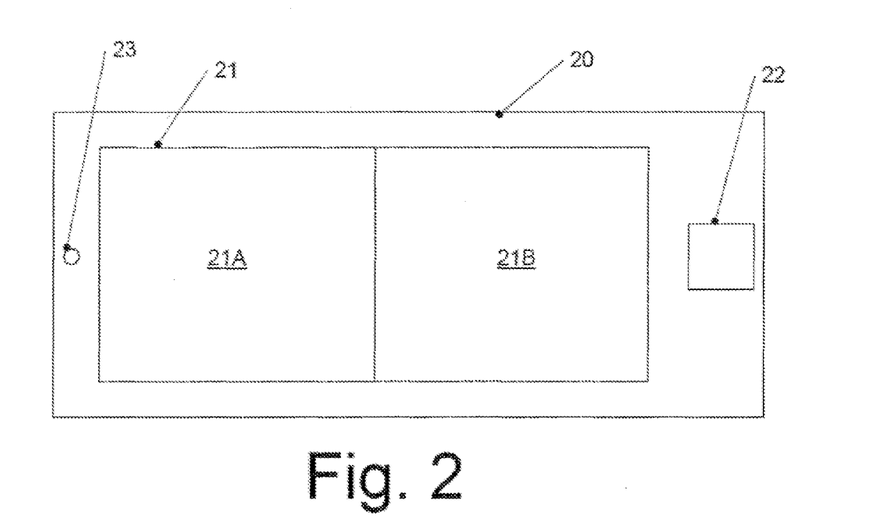
FIG. 2 a schematic outside view of a device according to an example embodiment, FIG. 3 a schematic view of a device according to an execution example with an optical attachment according to an example embodiment, FIG. 4 a schematic view of a device according to an execution example with an optical attachment according to another example embodiment, FIG. 5 a schematic image to clarify a perimetry measurement with a device according to an example embodiment, and FIG. 6 a flowchart for the purposes of illustration of a work method of a device according to an example embodiment, and FIG. 7 a device according to an example embodiment.

An example for an outside view of a mobile device 20 according to an example embodiment of the present invention is shown in FIG. 2. The mobile device 20 of FIG. 2 can correspond to the mobile computer device 10 of FIG. 1, for example, and is designed like a Smartphone in the example of FIG. 2. Depending on the type of Smartphone, the external view can differ from the one portrayed in FIG. 2. The mobile computer device 20 has a display 21, which can be realized as a touch-sensitive display (so-called touch-screen), in particular. The mobile computer device 20 in the portrayed example also has a control knob 22 and a camera 23. The camera 23 is also referred to as frontal camera. Another camera (not represented in FIG. 2) can be located on the opposite side (back) of the mobile computer device 20. The other camera on the rear housing part can be used to measure ambient light, for example. The mobile computer device 20 can comprise further elements not portrayed in FIG. 2, such as a headphones output, further operating elements, a loudspeaker, or a microphone.

As shown in FIG. 2, the display 21 can be divided into two areas 21A and 21B. In this case, for instance, the area 21A can be used to display an image for a left eye of a user and the area 21B to display an image for a view by a right eye of a user. Such a division doesn't take place in other execution examples, and the entire screen can be used for viewing with one eye, for example. As will be explained further below with reference to FIGS. 3 and 4, the mobile computer device 10 or 20 can be connected to a respective optical attachment, through which the display can be viewed with one or both eyes.

Through the division of the display as shown in FIG. 2, the left and the right eye can be tested separately by use of the diagnosis module 16, for example; such as by something only being displayed in the area 21A or only in the area 21B, and by that a respective feedback is evaluated by a user. In other examples, only one eye can be covered, for example and the display 21 can be viewed with the other eye.

In the areas 21A and 21B, images for the left and the right eye can be shown corresponding to a pupil distance, for example, to enable a stereo view. For instance, a distance of corresponding points can be adjusted such that it corresponds to the pupil distance of an adult human more or less, such as approx. 65 mm. In some example embodiments, the pupil distance can also be a parameter, so that the presentation may be adapted to the respective user and his/her pupil distance.

Mobile computer devices as presented in FIGS. 1 and 2 are frequently comparatively inexpensive as they are manufactured in large quantities. Nevertheless, high-quality displays, cameras, sensors, etc. are frequently installed in such devices.

As already explained, a possibility for a perimetry measurement is provided in example embodiments by a mobile computer device (e.g. 10 of FIG. 1 or 20 of FIG. 2) using a respective app, for example. By such a measurement, boundaries of the visual field and local scotomas may be determined on the one hand (which is also referred to as contour perimetry), a local sensitivity in the visual field can be determined additionally or alternatively, which is referred to as threshold perimetry. Optical stimuli in different areas and that possibly with a different brightness are hereby shown sequentially on a display of the computer device and are presented in the visual field that way. Measurements of the visual field for colors are also possible, by presenting colored light stimuli in the display. The perception of the stimuli is confirmed by a user, and is then recorded. In case of a classic perimeter as used by qualified personnel, for example, a person to be examined thereby looks at a hemispherical projection or screen surface. It is thereby possible to create light stimuli in all directions, for example up to a maximum angel of 90°, whereby a visual field of the person to be examined can be completely recorded.

Figure 3:
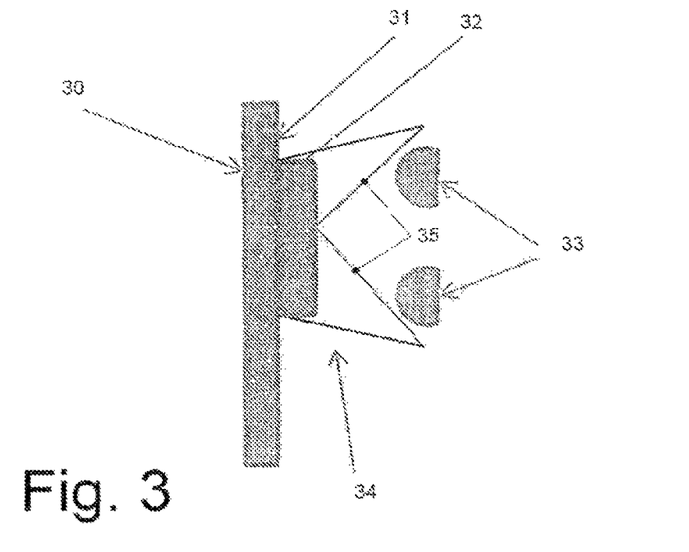
Figure 4:
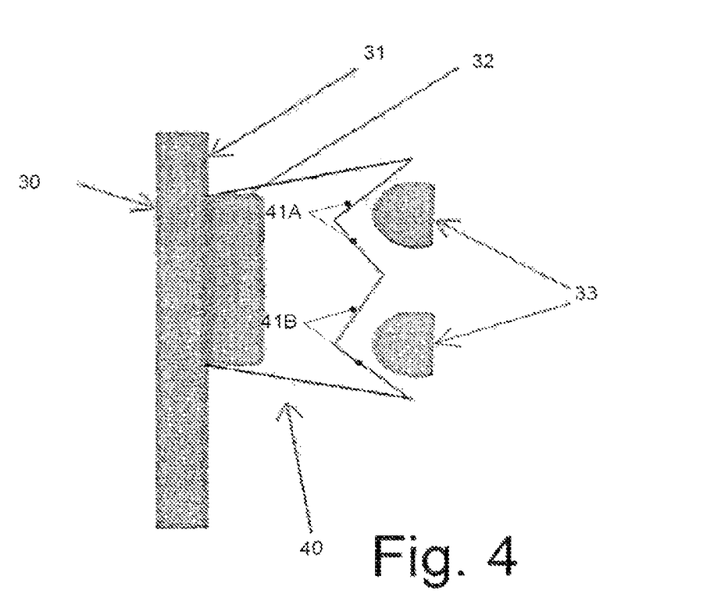

In some example embodiments, a mobile computer device such a Smartphone can then be connected to an optical attachment in a viewing device, for example, to enable the representation of optical stimuli in a desired area of the visual field. Examples for this are represented in FIG. 3 and FIG. 4. To avoid repetition, respective features in FIGS. 3 and 4 bear the same reference signs and will not be described repeatedly.

In FIGS. 3 and 4, provision is made for a mobile computer device 30, such as a Smartphone or a tablet computer, for example. The mobile computer device 30 comprises a display 32, on which light stimuli can be shown for a perimetry measurement. 31 describes a camera from the computer device (e.g. a frontal camera like the camera 23 of FIG. 2). By use of the camera 31, an image of one or two eyes 33 can be recorded possibly using suitable deflection mirrors and/or beam splitters. A viewing direction of an eye to be examined right then or of both eyes can thus be recorded. It can therefore be verified, for example, whether the viewing direction for the measurement of the visual field is correct, and/or light stimuli can be shown depending on the viewing direction. In other words, by using the camera 31, the actual position of the eyes or the eye can be controlled and/or registered when measuring the visual field, and/or measurements can be corrected. Knowing the eye position is an important parameter for the measurement of the actual visual field, as it can thus be determined, at which location light stimuli shown on the display 32 is supposed to be seen in relation to the viewing direction of the eye. Determining the viewing direction through the camera 31 can thus result in an increase of the accuracy of measurements in some example embodiments execution examples.

An optical attachment 34 is furthermore connected to the display 32 in the example embodiment of FIG. 3. In the example of FIG. 3, the display is depicted on a surface 35, for example, which makes it possible to have light stimuli appear in an entire visual field to be measured. In the example embodiment of FIG. 3, the surface 35 is designed such that the entire display or a large part thereof can be used to measure the visual field of an eye. To measure one eye, the other eye is then covered, for example.

However, in the example embodiment of FIG. 4, an optical attachment 40 is provided, which depicts the display 32 on separate patches 41A, 41B for the two eyes 33. The display 32 can be used divided for this purpose, as is explained by reference to FIG. 2, for example. Covering an eye is not necessary here, as each eye sees its own picture. It must be noted that light stimuli may appear virtually on areas different from the areas 35, 41A, and 41B shown depending on the type of the optical attachment. Other shapes particularly concave surfaces that the display 32 is depicted on (e.g. projected, transmitted) are also possible. The optical attachment can have the effect, for example, that an image of the display is transferred to a virtual hemisphere, e.g. with a radius between 350 and 400 mm. It can thus be achieved, for example that a visual field of >140 degrees can be measured, e.g. up to 70 degrees to both sides (in horizontal direction) and up to 30 degrees upwards and downwards. Other values are also possible, especially also values >400 mm for the radius of the hemisphere up to an "infinite radius", which would correspond to a two-dimensional image, while a three-dimensional visual field is obtained with a finite radius. In one example embodiment, the visual field of each eye is checked in at least 50, for example at least 100 positions (locations on the respective (virtual) surface.

Optical attachments such as the optical attachments 34 and 40 can be realized on the basis of a fiber optic and/or by using holograms, e.g. volume holograms, for example. Such optical attachments can be used to particularly realize a focused propagation of angles of the light.

Background lighting is for example approx. 15 cd/m$^2$ or less, in another example approx. 10 cd/m$^2$ or less. A room that the perimetry measurement is performed in can be darkened for this purpose, for example.

A camera from the mobile computer device can be used to measure the background lighting. For example, light density or illuminance can be captured with a camera intended on the back of a housing of a Smartphone or another mobile computer device due to on the ambient light. The mobile computer device can automatically determine, whether the ambient light is sufficiently low to perform the perimetry measurement. The perimetry measurement can be started selectively dependent on the light density or illuminance captured by use of the rear-sided camera of the mobile computer device due to the ambient light. Alternatively or additionally, a decision can be made whether measurements are discarded, depending on the light density or illuminance captured by the rear camera of the mobile computer device, which is generated by the ambient light. Alternatively, or additionally, information about a reliability of a measurement can be derived from the light density or illuminance captured with the rear camera of the mobile computer device, which is generated by the ambient light.

Alternatively or additionally, the device of FIG. 3 or 4 can essentially be connected light-tight to a head of a user, for example by use of an arrangement in a housing to be worn on the head or a different connection and/or fixation of the device on the head. For example, the device of FIG. 3 or 4 can also be attached to a tripod or a different support, and the person to be examined then sits in front of the device. Light-tight essentially means here, for example, that penetrating light produces a background lighting of less than 15 cd/m$^2$, for example less than 10 cd/m$^2$.

A camera from the mobile computer device can be used to measure the background lighting in the housing. For example, a light density or illuminance can be captured with a frontal camera of a Smartphone or a different mobile computer device due to the ambient light that is still present in the housing. The mobile computer device can determine automatically, whether the ambient light is sufficiently low to perform the perimetry measurement. The perimetry measurement can be started selectively depending on the light density or illuminance captured with the frontal camera of the mobile computer device. Alternatively or additionally, a decision can be made whether measurements are discarded, depending on the light density or illuminance captured by the frontal camera of the mobile computer device that is evoked by the ambient light in the housing. Alternatively, or additionally, information about the reliability of a measurement can be derived from the light density or illuminance captured with the frontal camera of the mobile computer device, which is evoked by the ambient light in the housing.

Figure 7:
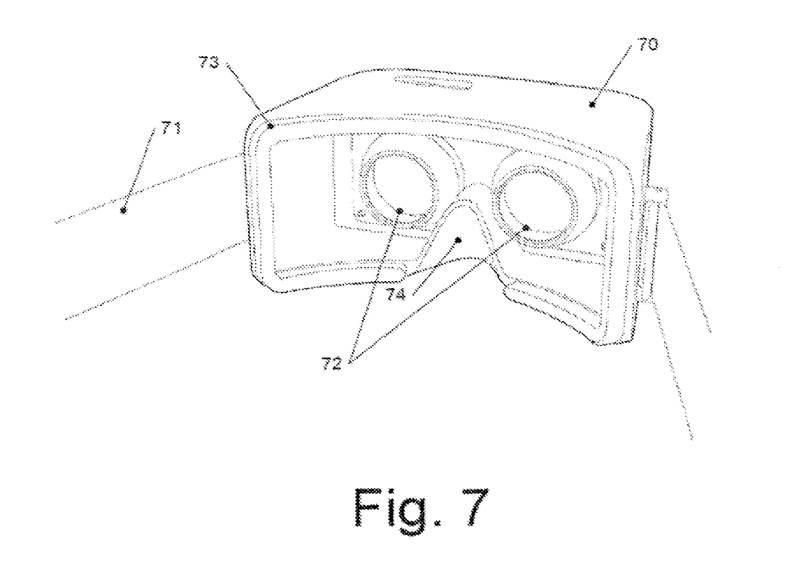

An example for such a housing 70 to be worn on the head is schematically represented in FIG. 7. The housing 70 can be attached to a head of a user by an elastic band 71 or a different device such as a suitable bracket. A mobile computer device such as a Smartphone can be inserted in a recording (not represented) in the housing 70 or can be connected to the housing differently. Using a seal 73 and an opening for the nose 74, the housing can essentially be attached to the head light-tight. The display of the mobile computer device can then be viewed through an optical attachment through openings 72 as described, whereby the optical attachment can also be arranged in the openings 72 in whole or in part.

Figure 5:
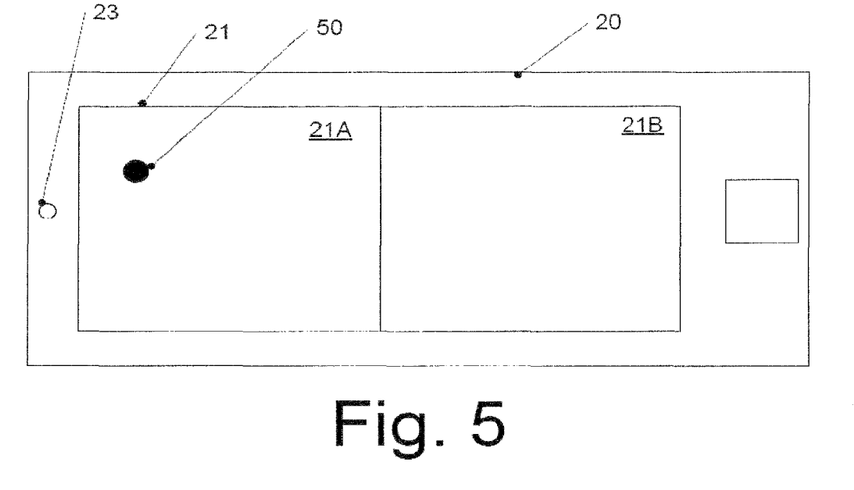

A perimetry measurement with a mobile computer device according to an example embodiment is schematically represented in FIG. 5, whereby the mobile computer device 20 of FIG. 2 is used here by way of example. To measure the visual field, sequential stimuli 50 are represented for the left eye (in the case represented in FIG. 5), meaning in the area 21A, for the right eye in the area 21B, or also for both eyes. The optical attachment of FIG. 4 can be used here, for example. With the optical attachment of FIG. 3, one eye can be covered and the stimulus 50 can be shown on the entire display 21. In the simple example of FIG. 5, the stimulus is simply a point in a specific place of the display 21. This way, the entire visual field or part therefore can be scanned and measured by the mobile computer device 20. Point 50 can thereby vary in terms of brightness or contrast to the background of the display 21, in terms of size, in terms of shape and/or in terms of color. If a user recognizes the portrayed stimulus, he confirms it. This can take place, for example, via speech input, which is captured through a microphone of the mobile computer device 20, through a head movement such as nodding, which is captured by an acceleration sensor or an inclination sensor, or through a gesture, which is captured through a camera of the mobile computer device 20. A confirmation through external devices, for example a button, a gamepad, or a different operating device that is connected to the device 20 via Bluetooth, for example, is also possible.

Such a perimetry measurement can be used to recognize local scotomas, for example. Such local scotomas are first compensated by the visual system of a person in many cases and are therefore often noticeable late, if just one eye is affected by scotomas. For an early recognition of illnesses that result in scotomas, a measurement of scotomas is therefore useful.

Illnesses that can result in such local scotomas are briefly explained in the following.

The age-related macular degeneration (AMD) is one of the most frequent eye diseases in the western world. In the so-called dry form, due to metabolite deposits, it can result in an impaired supply of the retina, to the cell death of retinal neurons, and thus insidiously to a worsening of the vision in the central area. In the aggressive, so-called wet form of the AMD, it results in fluid retention or a new growth of abnormal blood vessels as well as bleeding, which mostly leads to a dramatic loss of vision in the area of the macula. An early diagnosis and monitoring of the disease is meaningful in all cases.

In case of the diabetic retinopathy (DR), a retinal disease caused by diabetes mellitus, the result is damage to the retina due to changes in the blood vessels.

Glaucoma is a collective term of eye diseases with different causes. An important risk factor is an increased intraocular pressure. In case of glaucoma, it results in a damage of the optic nerve, which mostly leads to typical scotomas.

The eye diseases mentioned above mostly result in an irreparable worsening in vision. As there are treatments for most of these eye diseases in the meantime, an early diagnosis and a regular monitoring of the progression of the disease is advisable. Especially with the wet AMD, an effective treatment has been able to be performed for some time by an intravitreal injection of VEGF inhibitors (inhibitor against a growth factor). A close examination of the progression of the disease is advisable in this case, in particular.

A follow-up of the AMD can take place with a so-called Amsler grid, which is represented on the display of the mobile computer device, for example.

Mobile computer devices according to execution examples per the invention, such as Smartphone-based devices enable a simple perimetry measurement as explained above by reference to FIG. 5, which is not just performed at the ophthalmologist. In particular, opticians or general practitioners can also offer a "screening" using such a device. The result of the screening could be the recommendation to visit an ophthalmologist, in case of a conspicuous measurement result, for example. Patients with such a disease, particularly chronic disease, could additionally monitor their eye disease with an own device (or also a rental device) at home in a simple and relatively inexpensive manner. This particularly also applies to people who belong to risk groups, e.g. people with an increased intraocular pressure, glaucoma patients, or migraine patients with scotomas. The measurement results can be documented and can also be sent directly to a treating ophthalmologist (for example through a network interface like the network interface 14 of FIG. 1). Regular and close monitoring can thus be enabled.

Figure 6:
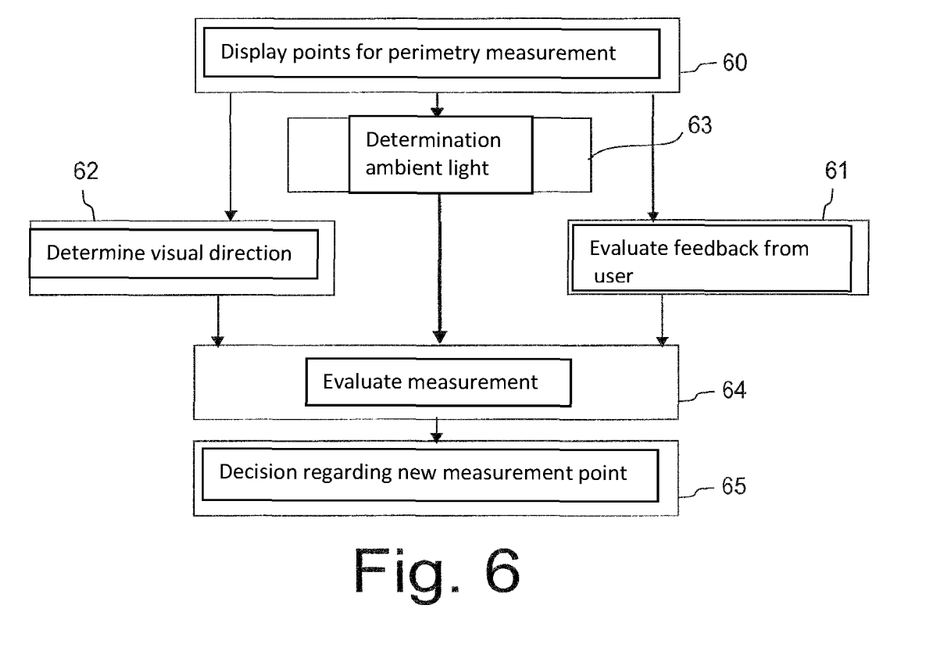

A flow diagram is shown in FIG. 6 as an illustration of a function of a mobile computer device like the devices according to an example embodiment by reference to FIGS. 1 to 5. For example, the steps shown in FIG. 6 can be implemented by a suitable computer program product, particularly by an app, such as by use of module 16 of FIG. 1, on a mobile computer device such as a Smartphone, a tablet, or the like.

In step 60, points or other light stimuli are shown on a display of a mobile computer device for the perimetry measurement, e.g. like explained by reference to FIG. 5. These light stimuli may be viewed with an optical attachment as explained by reference to FIGS. 3 and 4.

In step 61, a feedback from a user, e.g. whether the user saw the light stimulus, is then evaluated. The feedback can take place as described above, such as through speech, gestures, separate devices, etc.

In step 62, an eye position is determined by a camera from the mobile computer device as explained above, for example. Depending on the eye position, the measurement can be changed and/or the measurement result can be corrected.

An ambient light is determined in step 63. The rear camera of the mobile phone may be used for it, for example. Steps 61, 62, 64, and/or 65 can be executed depending on the specified ambient light.

The measurement can be evaluated in step 64. This can comprise a reliability assessment of the measurement depending on the ambient light and/or a correction of the measuring result depending on the eye position.

A decision for a further measurement can be made in step 65. It can thereby be determined automatically which light stimulus is supposed to be emitted through the display of the mobile computer device.

Steps 60-65 can be repeated to thereby scan a visual field.

By devices per the invention, perimetry measurements can thus be implemented in a simple manner, for example, by providing a respective computer program product such as an app for a smartphone or tablet, and/or by providing a respective optical attachment. Such apps can be updated by regular updates. A user can also be given recommendations as discussed, such as to visit an ophthalmologist, for example. Data with regard to the measurements can automatically be transmitted to a doctor or to another location or upon the request of a user. Many functions can thus be realized in a compact device relatively inexpensively, by using the infrastructure and a processing power of a mobile computer device such as a smartphone.

The example embodiments discussed above merely serve the illustration and are not to be interpreted restrictively.

The invention claimed is:

1. A system, comprising:
a mobile computer device comprising a display, a processor, and a memory with a program code stored therein, wherein the program code when executed on the processor, causes the processor to control the display to show light stimuli to perform a measurement of a visual field; and
an optical attachment operably connected to the display of the mobile computer device, wherein the optical attachment is configured to transfer an image with defined angle ratios shown on the display of the mobile computer device to at least one virtual hemisphere having a finite radius or in a visual field for an eye of a user as at least one virtual hemisphere having a finite radius.

2. The system according to claim 1, wherein the visual field comprises a three-dimensional visual field.

3. The system according to claim 1, wherein the mobile computer device further comprises an input device or is connectable to an input device;
wherein the program code, when executed on the processor further causes the processor to determine the visual field based on a feedback by the user through the input device in response to the display of the light stimuli.

4. The system according to claim 1, wherein the light stimuli are variable in terms of at least one of shape, size, color, brightness, or contrast.

5. The system according to claim 1, wherein the computer device further comprises a camera, can be connected with a camera or both comprises a camera and can be connected with a camera; and wherein the mobile computer device is configured to determine a viewing direction of a user based on a camera image.

6. The system according to claim 5, wherein the mobile computer device is configured to perform the determination of the visual field depending on the determined viewing direction.

7. The system according to claim 1, further comprising a network interface configured to exchange data with medical professionals.

8. The system according to claim 1, wherein the program code when executed on the processor, causes an image for a left eye of a user to be displayed on a first part of the display and an image for a right eye of a user to be displayed on a second part of the display.

9. The system according to claim 1, wherein the mobile computer device comprises one of a Smartphone or a tablet computer.

10. The system according to claim 1, wherein the finite radius of the virtual hemisphere is between 350 and 400 mm.

11. The system according to claim 1, wherein the finite radius of the virtual hemisphere is more than 400 mm.

12. The system according to claim 1, wherein the optical attachment further comprises at least one of a hologram, a volume hologram, or a fiber optic.

13. The system according to claim 1, wherein the system is structured to be connectable light-tight with a head of a user in an essentially light-tight manner.

14. The system according to claim 1, wherein the system is fixable relative to a head of a user.

15. The system according to claim 14, wherein the system is fixable through a housing that has a recording for the mobile computer device.

16. The system according to claim 1, wherein the mobile computer device comprises a camera that measures ambient light when measuring the visual field.

17. The system according to claim 16, wherein the mobile computer device is configured to determine by use of a luminance captured by the camera whether the measurement of the visual field is feasible.

18. An optical attachment for connecting to a mobile computer device, wherein the optical attachment is configured to transfer an image shown on a display of the mobile computer device with defined angle ratios to at least one virtual hemisphere having a finite radius or in a visual field for one eye of a user as at least one virtual hemisphere having a finite radius.

19. The optical attachment according to claim 18, wherein the visual field comprises a three-dimensional visual field.

20. The optical attachment according to claim 18, wherein the finite radius of virtual hemisphere is between 350 mm and 400 mm.

21. The optical attachment according to claim 18, wherein the finite radius of the virtual hemisphere is more than 400 mm.

22. The optical attachment according to claim 18, wherein the optical attachment comprises at least one of a hologram, a volume hologram, or a fiber optic.

23. A kit to be utilized with a mobile computer device, comprising:
- an optical attachment for connecting to the mobile computer device;
- wherein the optical attachment is configured to transfer an image shown on a display of the mobile computer device with defined angle ratios to at least one virtual hemisphere having a finite radius or in a visual field for one eye of a user as at least one virtual hemisphere having a finite radius; and
- a non-transitory computer readable data storage medium that is not a carrier wave or signal, comprising instructions to determine a visual field with a program code that when executed on a processor causes the processor to actuate a display to show light stimuli to perform a measurement of a visual field.

24. The kit according to claim 23, wherein the program code, when executed on the processor further causes the processor to determine the visual field based on a feedback from the user through the input device in answer to the display of the light stimuli.

* * * * *

UNITED STATES PATENT AND TRADEMARK OFFICE
CERTIFICATE OF CORRECTION

PATENT NO. : 10,299,674 B2
APPLICATION NO. : 15/512570
DATED : May 28, 2019
INVENTOR(S) : Nico Correns et al.

It is certified that error appears in the above-identified patent and that said Letters Patent is hereby corrected as shown below:

In the Specification

Column 7, Line 44, delete "intended"

Column 7, Line 45, delete "on"

Signed and Sealed this
Seventeenth Day of March, 2020

Andrei Iancu
*Director of the United States Patent and Trademark Office*